(12) United States Patent
Gagneur et al.

(10) Patent No.: US 8,156,587 B2
(45) Date of Patent: Apr. 17, 2012

(54) HOLDING DEVICE

(75) Inventors: Klaus Gagneur, Möhrendorf (DE);
Volker Schmidt, Effeltrich (DE);
Robert Wirth, Hersbruck (DE)

(73) Assignee: Siemens Aktiengesellschaft, Munich (DE)

( * ) Notice: Subject to any disclaimer, the term of this patent is extended or adjusted under 35 U.S.C. 154(b) by 701 days.

(21) Appl. No.: 12/008,688

(22) Filed: Jan. 11, 2008

(65) Prior Publication Data

US 2008/0172793 A1 Jul. 24, 2008

(30) Foreign Application Priority Data

Jan. 18, 2007 (DE) .......................... 10 2007 002 721

(51) Int. Cl.
*A47C 16/00* (2006.01)
(52) U.S. Cl. .............................................. 5/646; 5/658
(58) Field of Classification Search ............... 5/623, 621, 5/646, 662, 658, 503.1
See application file for complete search history.

(56) References Cited

U.S. PATENT DOCUMENTS

| 1,915,985 | A | * | 6/1933 | Edwards | 340/286.07 |
| 2,259,757 | A | * | 10/1941 | Longfellow | 602/34 |
| 4,827,943 | A | * | 5/1989 | Bornn et al. | 600/481 |
| 5,537,702 | A | * | 7/1996 | Brown-Milants et al. | 5/632 |
| 5,736,702 | A | * | 4/1998 | Roberts et al. | 200/81 H |
| 6,012,182 | A | * | 1/2000 | Allen et al. | 5/81.1 R |
| 6,486,792 | B1 | * | 11/2002 | Moster et al. | 340/4.11 |
| 7,017,209 | B1 | * | 3/2006 | De Jong et al. | 5/601 |
| 2006/0019800 | A1 | | 1/2006 | Berger et al. | |
| 2009/0121863 | A1 | * | 5/2009 | Prior | 340/539.12 |

FOREIGN PATENT DOCUMENTS

DE 10 2004 024 097 A1 12/2005

* cited by examiner

*Primary Examiner* — Fredrick Conley

(57) ABSTRACT

The invention relates to a holding device for supporting the hands of a patient resting on an examination couch. In accordance with the invention, the holding device for supporting the hands of a patient resting on an examination couch comprises gripping zones which are distanced from one another, said gripping zones each being grippable with a hand of the patient, with the holding device being moveable independently of further devices surrounding the patient.

8 Claims, 2 Drawing Sheets

HOLDING DEVICE

CROSS REFERENCE TO RELATED APPLICATIONS

This application claims priority of German application No. 10 2007 002 721.6 filed Jan. 18, 2007, which is incorporated by reference herein in its entirety.

FIELD OF THE INVENTION

The invention relates to a holding device for supporting the hands of a patient lying on an examination couch

BACKGROUND OF THE INVENTION

A patient lies on an examination couch during a plurality of different examinations. By way of example, in the case of examinations for medical-diagnostic imaging or also with spectroscopic examinations, the patient must spend up to 30 minutes or longer in a reclining position. In this process, the aim is often for the patient not to move or only move slightly, since otherwise the examination results may be falsified or rendered unusable.

No standard specification previously existed for this, where the patient is able to support his/her hands in a risk-free fashion. With examinations in which the examination couch has to be moved through or into a medical examination device for instance, such as in the case of magnetic resonance examinations or computer tomography examinations, a finger supported laterally on the examination couch or another region of the hand may suffer bruising. In many cases, this may even result in a bone in the hand being broken. Such cases are known from the field.

As countermeasures, warnings were in the first instance previously printed in the instruction manual of the examination devices for instance, which however generally have to be passed onto the patient by the personnel responsible for the examination, in order to indicate their effect. This can be easily forgotten, particularly in the case of hectic operational conditions. Structural measures such as covers or so-called guide rods are known as further countermeasures, with which examination couches and/or examination devices can be retrofitted, so as to prevent the hands from getting caught at the sides of the examination couch. These structural measures are however mostly very complicated and thus very expensive.

Folding the hands across the stomach for instance also often represents an unsuitable manner of supporting the hands. On the one hand, in the case of some examination modalities, the possibility exists of precisely covering the region of the body of the patient to be examined in this position. On the other hand, this position can also endanger the patient in another fashion. Magnetic resonance examinations for instance therefore do not allow the hands to be folded or supported on one another and/or directly next to one another since this results in a so-called loop. In other words, such a position could allow the body to absorb high frequency emissions of the magnetic resonance device and to heat up significantly in places as a result, thereby leading to burns.

The formation of such inductive loops out of body parts is a serious problem. For instance, DE 10 2004 024 097 A1 specifies a method for optimizing the arrangement of a patient in a clinical scanner. The aim here is in particular to prevent loops by optical monitoring.

U.S. Pat. No. 5,537,702 discloses a cushion, which holds and fixes the arms and head of a patient during an imaging examination. In this way, the arms are fixed next to the head of the patient by means of ties. The wrists can also be fixed with further ties. These fastenings oblige the patient to hold his/her arms and hands in a fixed predetermined position.

US 2006/0019800 A1 discloses a device for the positioning of forearms for medical imaging or analysis. In this way, the lower arms are fastened in support guides, which force the forearms into a predetermined position. Rotatable handles are provided for the hands, said handles allowing the forearms and wrists of a patient to be examined with different, fixedly adjustable rotation angles. The patient is also clamped here into the device such that he has to retain a certain position.

The lack of a standard specification, where the patient is able to support his/her hands in a risk-free manner, results time and again in uncertainty and discomfort or even in injuries to the patient.

SUMMARY OF THE INVENTION

It is thus the object of the present invention to increase the well-being and the safety of the patients during a plurality of different examinations on an examination couch.

The object is achieved by the features specified in the claims. Accordingly, a holding device is provided to support the hands of a patient lying on an examination couch, with the holding device comprising gripping zones which are distanced from one another, said gripping zones each being grippable with a hand of the patient, with the holding device being moveable independently of further devices surrounding the patient.

The invention is based on the following concepts.

Examinations, in particular more lengthy examinations, represent a stress situation for most patients, with the majority of patients perceiving it to be comforting and secure when they find support for their hands. The examination couches are however often just as wide as the body of the patient and thus offer no support surface for the arms and hands. Nor is any other space provided for the hands. It is frequently observed that the patient folds his/her hands across the stomach without being requested to do so or holds onto the side edges of the examination couch. These appear to be comfortable and comforting positions for the patient. However, these positions are not always risk-free, as was previously described. The holding device according to the invention allows a defined support space for his/her hands to be offered to the patient, which neither negatively influences the examination nor endangers the patient. Instead, a safe feeling is conveyed to the patient. An ergonomic design of the gripping zones allows the holding device to be used unambiguously and to also be implemented without any previous instruction. The holding device according to the invention is suited to a plurality of medical examinations in which the patient lies on an examination couch. Furthermore, the holding device can also be easily retrofitted in older examination devices.

Further advantageous developments of the invention are characterized by the features of the subclaims.

In a particularly advantageous embodiment, the holding device includes a touch protection system which prevents the hands of a patient from coming into contact with other body parts of the patient. In particular, the hands are prevented from being touched. This increases the safety of the patient in a simple fashion by effectively preventing loops.

Expediently the width of the holding device does not exceed the width of the examination couch. As a result, the holding device is also suited to examinations, in which the examination support has to be moved through or into a medical examination device, such as with magnetic resonance examinations or computer tomography examinations, without a collision of the holding device with the examination device being expected.

The holding device can be moved at least temporarily independently of further devices surrounding the patient. As a result, this ensures a particularly multifunctional usability and a non-complicated transportability. Furthermore, the patient can already be given instructions prior to the examination, for instance in a waiting room, in how to use the holding device, so that the examination can be started immediately without further delays as a result of explanations.

A further advantage of a free moveability of the holding device lies in the large number of possible positions on the couch. Depending on the examination region or comfort of the patient, there is a plurality of possible holding positions, from arms stretched out for instance next to the head to a holding position in the region of the thigh of the patient.

In a further advantageous variant of the invention, the holding device is at least partially connected to a further device surrounding the patient by means of a flexible connection. A signal or data exchange between the holding device and the further device surrounding the patient is thus enabled for instance without restricting the plurality of possible holding positions.

The holding device preferably includes signaling means, so that the patient is able to issue signals if necessary, for example a call to the personnel responsible for the examination. A call function of this type is advised particularly in the case of MR examinations, since the patient often has no other possibility of communicating with persons outside the MR device.

The signal sensors for triggering a call function of this type are expediently arranged in the vicinity of the gripping zones of the holding device, so that the patient is able to trigger the call function, without having to reach for it.

The signaling means of the holding device can advantageously include a pneumatic and/or hydraulic switch, which can be connected to a plug connector of the examination couch as a trigger of a call function for instance in an uncomplicated fashion instead of a conventional pneumatic or hydraulic squeeze bulb.

It is easily possible for a patient to be able to transmit further, in particular also more complicated signals, for instance feedback to specific questions or stimuli, in that the signaling means include at least one further sensor. This additional sensor can also be embodied as a piezo-electric sensor.

All components of the holding device are preferably MR compatible and/or x-ray compatible. This thus ensures that they can be used with the largest possible number of different examinations. Incidentally, the holding device is provided such that it can be easily cleaned, is kind to skin, anti-allergic and if necessary can be disinfected and/or sterilized.

In a further embodiment, the holding device is embodied in a flexible fashion. An ergonomic adjustment to the physiology of different patients is thus enabled in a simple fashion.

BRIEF DESCRIPTION OF THE DRAWINGS

Further advantages and details of the present invention result from the exemplary embodiments described below as well as with reference to the drawings. Here, the detailed examples do not represent any restriction of the invention, in which.

DETAILED DESCRIPTION OF THE INVENTION

Figure 1:
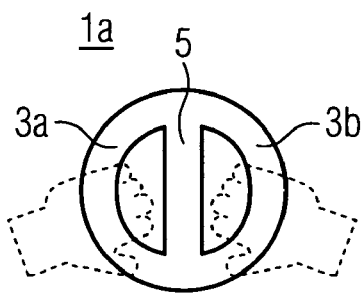
FIG. 1 shows a first possible design of a holding device according to the invention.

FIG. 1 shows a first design of a holding device 1a according to the invention having an essentially annular basic form. In this way, "annular" is not only understood to mean a purely torus-shaped body, but rather also all further loop-type closed shapes, such as for instance tori which are deformed to form an oval, an ellipse or a polygon or also other shapes which are formed for instance by bending a cylinder or hollow cylinder and are if necessary closed. The cross-section of the cylinder and/or torus can vary here.

A memory-type contact protection system 5 divides the holding device 1a into two parts, which each include a gripping zone 3a and 3b, which can be ergonomically gripped. Two hands are shown schematically in one possible gripping position.

Figure 2:
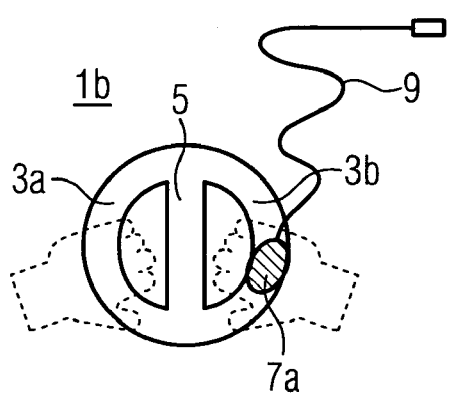
FIG. 2 shows an embodiment of the first possible design of the holding device having signaling means.

FIG. 2 shows a holding device 1b, with identically acting parts being provided accordingly with the same reference characters as in FIG. 1. The holding device 1b differs from the holding device 1a in that a signal sensor 7a is arranged on the gripping zone 3b, said signal sensor being able to transmit signals by way of a signal link 9. A signal sensor 7a of this type can also be additionally arranged for instance on the gripping zone 3a (not shown). Possible signal sensors 7a are pneumatic or hydraulic switches for instance. These are particularly suited to triggering a call function. In another embodiment, at least one signal sensor 7a can also be a piezo sensor, which if necessary is shielded against electromagnetic fields. In this case, the signal connection 9 is also shielded against electromagnetic fields. The number of signal sensors 7a and signal connections 9 can vary depending on requirements, but should not be so large that simple operation is no longer possible, and faulty operations are anticipated.

Figure 3:
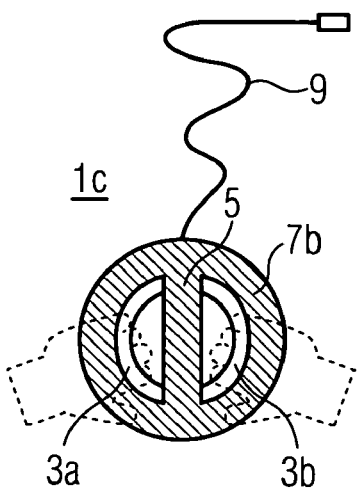
FIG. 3 shows a further possible embodiment of the first design of the holding device having signaling means.

FIG. 3 shows a further embodiment of an inventive holding device 1c, with identically acting parts being provided accordingly with the same reference characters as in FIG. 1 and FIG. 2. In this embodiment, the holding device 1c includes a signal sensor 7b on its outwardly pointing region. As a result, a signal emission is possible from each gripping position. Further signal sensors 7a can be arranged on the interior (not shown).

Figure 4:
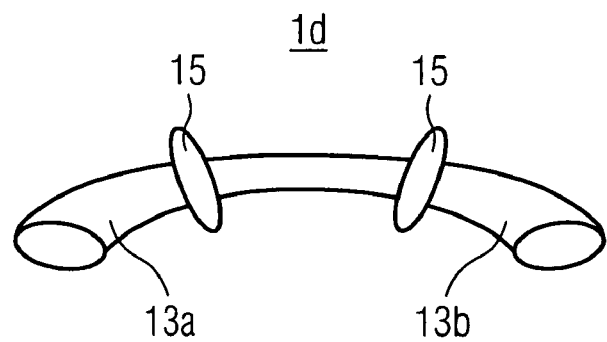
FIG. 4 shows a second possible design of a holding device according to the invention and FIG. 5 shows an embodiment of the second possible design of the holding device having signaling means.

FIG. 4 shows a holding device 1d in a further possible design. The holding device 1d comprises an essentially rod-like basic form, the ends of which each form a gripping zone 13a, 13b. Rod-shaped is understood here to mean any longish, possibly slightly bent shape with two outer ends. The ergonomically formed gripping zones 13a and 13b are distanced from one another to such a degree that the hands of the patient do not touch when gripping the gripping zones. As a further protection, two bulges on the holding device 1d form a further touch protection system 15. In another embodiment, only one bulge is provided as a touch protection system 15 (not shown).

Figure 5:
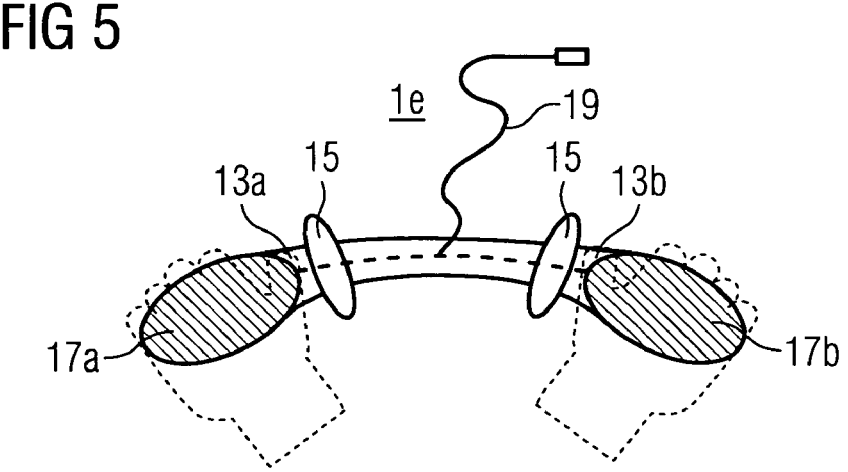

FIG. 5 shows a holding device 1e, with identically acting parts being accordingly provided with the same reference characters as in FIG. 4. The holding device 1e differs from the holding device 1d in that the gripping zones 13a, 13b include signal sensors 17a, 17b, which can transmit signals by way of a signal link 19 shielded if necessary against electromagnetic fields. The signal link runs for instance within the rod-like holding device and escapes outwards, e.g. in the center of the holding device across a T-connection. It is also conceivable for only one of the gripping zones 13*a*, 13*b* to comprise a signal sensor 17*a* and/or 17*b*. Further, possibly different signal sensors can also be implemented in different arrangements, as already in the embodiment in FIG. 2. One possible gripping position is illustrated by way of the hands shown with a dashed line.

A particularly cost-effective embodiment which can be realized in a simple fashion is given by an optionally strengthened T-connection of a pneumatic or hydraulic signal connection, with the two ends of the T-stripe forming the gripping zone. A contact protection can be realized for instance by bulges on the tube-like pneumatic or hydraulic signal line.

The invention claimed is:

1. A holding device for supporting a hand of a patient resting on an examination couch, comprising:
   a gripping zone that is griped by the hand of the patient;
   a signaling device arranged in a vicinity of the gripping zone for generating a signal; and
   a signal link connected to the signaling device for transmitting the signal,
   wherein the holding device is flexible,
   wherein the holding device comprises an essentially rod-like basic form with two outer ends,
   wherein the rod-like basic form is a longish shape and each of the two outer ends comprises a gripping zone gripped by one hand of the patient,
   wherein the rod-like basic form comprises two bulges as a touch protection system that prevents the hand of the patient from contacting with other body parts of the patient, and
   wherein the holding device is moved independently with a further device surrounding the patient.

2. The holding device as claimed in claim 1, further comprising a touch protection system that prevents the hand of the patient from contacting with other body parts of the patient.

3. The holding device as claimed in claim 1, wherein the signaling device comprises a signal sensor for triggering a call function.

4. The holding device as claimed in claim 3, wherein the signal sensor comprises a pneumatic or hydraulic switch.

5. The holding device as claimed in claim 3, wherein the signal sensor comprises a piezo sensor.

6. The holding device as claimed in claim 1, wherein components of the holding device are MR compatible or x-ray compatible.

7. The holding device as claimed in claim 1, wherein the holding device comprises two gripping zones that are distanced from one another.

8. A method for supporting a hand of a patient resting on an examination couch, comprising:
   providing a holding device;
   arranging a gripping zone in the holding device;
   gripping the hand of the patient by the gripping zone;
   arranging a signaling device in a vicinity of the gripping zone for generating a signal; and
   transmitting the signal by a signal link connected to the signaling device,
   wherein the holding device is flexible,
   wherein the holding device comprises an essentially rod-like basic form with two outer ends,
   wherein the rod-like basic form is a longish shape and each of the two outer ends comprises a gripping zone gripped by one hand of the patient,
   wherein the rod-like basic form comprises two bulges as a touch protection system that prevents the hand of the patient from contacting with other body parts of the patient, and
   wherein the holding device is moved independently with a further device surrounding the patient.

* * * * *